(12) United States Patent
Troy

(10) Patent No.: US 7,125,956 B2
(45) Date of Patent: Oct. 24, 2006

(54) COMPOUNDS WHICH PREVENT NEURONAL CELL DEATH AND USES THEREOF

(75) Inventor: Carol M. Troy, Hastings-on-Hudson, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 499 days.

(21) Appl. No.: 10/665,668

(22) Filed: Sep. 19, 2003

(65) Prior Publication Data

US 2005/0059603 A1 Mar. 17, 2005

Related U.S. Application Data

(62) Division of application No. 08/610,220, filed on Mar. 4, 1996, now Pat. No. 6,635,738.

(51) Int. Cl.
C07K 1/00 (2006.01)
C07K 14/00 (2006.01)
A61K 38/00 (2006.01)

(52) U.S. Cl. .................. 530/300; 530/350; 514/2
(58) Field of Classification Search ............... 530/300, 530/350; 514/2
See application file for complete search history.

(56) References Cited

U.S. PATENT DOCUMENTS

| 5,672,500 | A | 9/1997 | Litwack et al. |
| 6,635,738 | B1 | 10/2003 | Troy et al. |
| 2002/0044931 | A1 | 4/2002 | Troy et al. |

FOREIGN PATENT DOCUMENTS

| EP | 425212 | 5/1991 |
| EP | 533350 | 5/1999 |

OTHER PUBLICATIONS

Barinaga, M. (1994) Cell Suicide: By ICE, Not Fire. *Science* 263.: 754-756.
Casciola-Rosen, L.A. et al. (1994) Specific Cleavage of the 70-kDa Protein Component of the U1 Small Nuclear Ribonucleoprotein Is a Characteristic Biochemical Feature of Apoptotic Cell Death. *J. Bio. Chem.* 269 (49) : 30757-30760.
Derossi, D., et al. (1996) Cell Internalization of the third helix of *Antennapedia* homeodomain is receptor-independent. *J. Biol. Chem.* 211, 18188-93.
Duggan, M.E. et al. (1995) Non-Peptide Fibrinogen Receptor Antagonists. 7. Design and Synthesis of a Potent, Orally Active Fibrinogen Receptor Antagonist. *J. of Med. Chem.* 38(17) : 3332-3341.
Enari, M., Hug, H. and Nagata, S. (1995) Involvement of an Ice-like protease in Fas-mediated apoptosis. *Nature* 375:78-81.
Fernandes-Alnemri, T., Litwack, G. and Alnemri, E. S. (1995) Mch2, a New Member of the Apoptotic Ced-3/Ice Cysteine Protease Gene Family. *Cancer Res.* 55-2737-2742.
Koivunen, E., Gay, D.A. and Ruoslahti, E. (1993) Selection of Peptides Binding to the oPi Integrin from Phage Display Library. *J. of Biol. Chem.* 27:20205-20210.
Los, M. et al. (1995) Requirement of an ICE/CED-3 protease for Fas/APO-1-mediated apoptosis. *Nature* 375:81-83.
Luo, A.-M. et al. (Nov. 1993) Antigen Mimicry in Autoimmune Disease, Sharing of Amino Acid Residues Critical for Pathogenic T Cell Activation. AIT?. *Soc. for Clin. Invest.* 92:2117-2123.
Mashima, T. et al. (1995) Aspartate-Based Inhibitor of Interleukin-1 (3-Converting Enzyme Prevents Antitumor Agent-Induced Apoptosis in Human Myeloid Leukemia U937 Cells. *Biochem. and Biophys. Res. Comm.* 209 (3):907-915.
Milligan, C.E. et al. (1995) Peptide Inhibitors of the ICE Protease Family Arrest Programmed Cell Death of Motoneurons In Vivo and In Vitro. *Neuron* 15:385-393.
Munday, N.A. et al. (1995) Molecular Cloning and Pro-apoptotic Activity of ICE $_{rel}$ II and ICE $_{rel}$ III, Membersof the ICE/CED-3 Family of Cysteine Proteases. *J. of Biol. Chem.* 270 (26) : 15870-15876.
Prochiantz, A. (1996) Getting hydrophilic compounds into cells: lessons from homeopeptides. *Curr. Opin. Neurobiol.* 6:629-34.
Troy, C. -M. , . et al. (1996) Downregulation- of Cu/Zn superoxide dismutase leads to cell death via the nitric oxide-peroxynitrite pathway. *J. Neurosci.* 16:253-61.
Wang, L. et al. (1994) Ich-1, an Ice/ced-3-Related Gene. Encodes Both Positive and Negative Regulators of Programmed Cell Death. *Cell* 78:739-750.
Wang, X. et al. (1995) Purification of an Interleukin-13Converting Enzyme-related cysteine Protease That Cleaves Sterol Regulatory Element-binding Proteins between and Leucine Zipper and Transmembrane Domains. *J. of Biol. Chem.* 270(30) :18044-18055.
Xuan, J.-W. et al. (1995) Site-Directed Mutagenesis of the Arginine-Glycine-Aspartic Acid Sequence in Osteopontin Destroys Cell Adhesion and Migration Functions. *J. of Cell. Biochem.* 57:680-690.

Primary Examiner—Mark Navarro
(74) Attorney, Agent, or Firm—John P. White, Esq.; Cooper & Dunham LLP

(57) ABSTRACT

The present invention provides for a compound having the structure: $(AA_1)_n$-Cys-$(AA_2)_m$ wherein n=0,1,2,3,4 or 5 and m=0,1,2,3,4 or 5, provided the sum of (n+m) is greater than or equal to two and less than or equal to five, if n=1, $(AA_1)_n$=Ala-, if n=2, $(AA_1)_n$=Gln-Ala-, if n≧3, $(AA_1)_n$= $(Xaa)_p$-Gln-Ala-, and Xaa=any amino acid and wherein if n=n3, p=1, if n=4, p=2, if n=5, p=3, if m=1, $(AA_2)_m$=-Arg, if m=2, $(AA_2)_m$=-Arg-Gly, if m≧3, $(AA_2)_m$=-Arg-Gly-$(Xaa)_q$, wherein if m=3, q=1, if m=4, q=2, if m=5, q=3. The present invention provides for a method of inhibiting cell death and a method for alleviating symptoms of a neurodegenerative disorder in a subject.

7 Claims, 9 Drawing Sheets

COMPOUNDS WHICH PREVENT NEURONAL CELL DEATH AND USES THEREOF

This application is a divisional application of U.S. Ser. No. 08/610,220, filed Mar. 4, 1996, now U.S. Pat. No. 6,635,738 the contents of which are hereby incorporated by reference.

The invention disclosed herein was made with Government support under NIH Grants No. MDA CU 50898501A1, NS 15076R35-AG10963, PO1-AG07232, RR00645 and P50-AG-08702 from the Department of Health and Human Services. Accordingly, the U.S. Government has certain rights in this invention.

BACKGROUND OF THE INVENTION

Throughout this application, various publications are referenced by author and date. Full citations for these publications may be found listed alphabetically at the end of the specification immediately preceding the Sequence Listing. The disclosures of these publications in their entireties are hereby incorporated by reference into this application in order to more fully describe the state of the art as known to those skilled therein as of the date of the invention described and claimed herein.

Members of the family of cysteine proteases related to the interleukin 1β converting enzyme (ICE) have been shown to be necessary for programmed cell death in a number of biological systems (Yuan et al., 1993). For example, mutations of the ICE homologue, ced3, inhibit cell death which normally occurs during development in *C. elegans* (Hengartner et al., 1992) and overexpression of ICE or the ICE-like proteases NEDD-2/ICH-1 and Yama/apopain/CPP32 induces apoptosis in primary neurons, rat fibroblasts and insect cells (Gagliardini et al., 1994; Miura et al., 1994; Wang et al., 1994; Kumar et al., 1994; and Fernandes-Alnemri et al., 1994). Mice lacking ICE are resistant to apoptosis induced by Fas antibody. In the mammary gland, ICE mRNA is expressed during involution, when apoptosis occurs in this tissue. The pox virus product crmA, a serpin-like pseudosubstrate for ICE, protects sensory neurons and fibroblasts from trophic factor withdrawal-induced death (Gagliardini et al., 1994 and Miura et al., 1994), while Fas/APO-1 mediated apoptosis is blocked by the inhibitory peptide YVAD (Seq. I.D. No. 7), as well as crmA (Tewari and Dixit, 1995; Enari et al., 1995; Los et al., 1995; and Tewari et al., 1995). Normal motor neuron loss in development is also blocked by YVAD (Seq. I.D. No. 7), a pseudosubstrate which mimics the pro-IL-1β cleavage site and thus inhibits ICE-like proteases (Milligan et al., 1995). While ICE cleaves pro-IL-1β to produce IL-1β, the role of IL-1β itself in apoptosis is unresolved and it has been suggested that other substrates may be critical in cell death (Lazebnik et al., 1994; Tewari et al., 1995; and Nicholson et al., 1995).

Although many researchers have focused their efforts on the identification and isolation of an inhibitor of the family of cysteine proteases related to the ICE enzyme, there has been little success in this area. Many of these research strategies involve searching through a multitude of compounds and agents which are extrinsic to the ICE protein normally. However, the present invention deviates from the established search strategies and provides for the surprising discovery that use of a piece of the ICE enzyme itself successfully inhibits ICE and thus prevents neuronal cell death.

SUMMARY OF THE INVENTION

This invention provides for a compound having the structure: $(AA_1)_n$-Cys-$(AA_2)_m$, wherein n=0,1,2,3,4 or 5 and m=0,1,2,3,4 or 5, provided the sum of (n+m) is greater than or equal to two and less than or equal to five, if n=1, $(AA_1)_n$=Ala-, if n=2, $(AA_1)_n$=Gln-Ala-, if n≧3, $(AA_1)_n$=$(Xaa)_p$-Gln-Ala-,and Xaa=any amino acid and wherein if n=3, p=1, if n=4, p=2, if n=5, p=3, if m=1, $(AA_2)_m$=-Arg, if m=2, $(AA_2)_m$=-Arg-Gly, if m≧3, $(AA_2)_m$=-Arg-Gly-$(Xaa)_q$, wherein if m=3, q=1, if m=4, q=2, if m=5, q=3. The present invention provides for a method of inhibiting cell death and a method for alleviating symptoms of a neurodegenerative disorder in a subject.

Legend: a=+NGF (control cells); b=−NGF+V-ICE$_{inh}$ (2 additions); c=−NGF+V-ICE$_{inh}$ (1 addition); d=−NGF. Data in all cases are presented as means±SEM (n=3–5).

FIGS. 3A, 3B, 3C and 3D. V-ICE$_{inh}$ protects cultured sympathetic neurons from apoptotic death induced by NGF-withdrawal. (A) Time course of protection of sympathetic neurons by V-ICE$_{inh}$ (50 nM). (B–D) Photomicrographs of sympathetic neurons: (B) NGF; (C) anti-NGF; (D) anti-NGF+V-ICE$_{inh}$ (50 nM). Sympathetic neuron cultures were prepared from 2 day old rat pups. On the sixth day following plating, NGF was removed by washing the cultures three times with RPMI 1640 medium plus 10% horse serum, followed by the addition of medium containing anti-mouse NGF (1:200). V-ICE$_{inh}$ (50 nM) was added to certain cultures as indicated. Numbers of surviving neurons were assessed by counting the number of intact, phase bright neurons in each well by strip counting. This determination was made on the initial day of NGF deprivation and then on subsequent days. Results are expressed as the percentage of neurons present relative to that present immediately following NGF withdrawal.

Figure 4A:
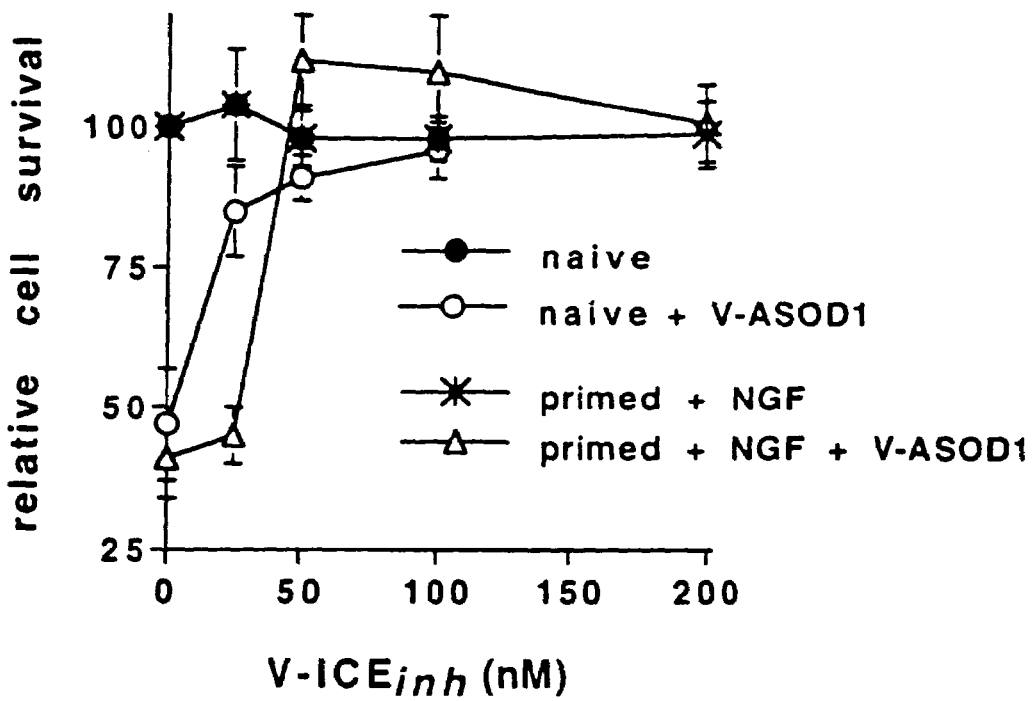
Figure 4B:
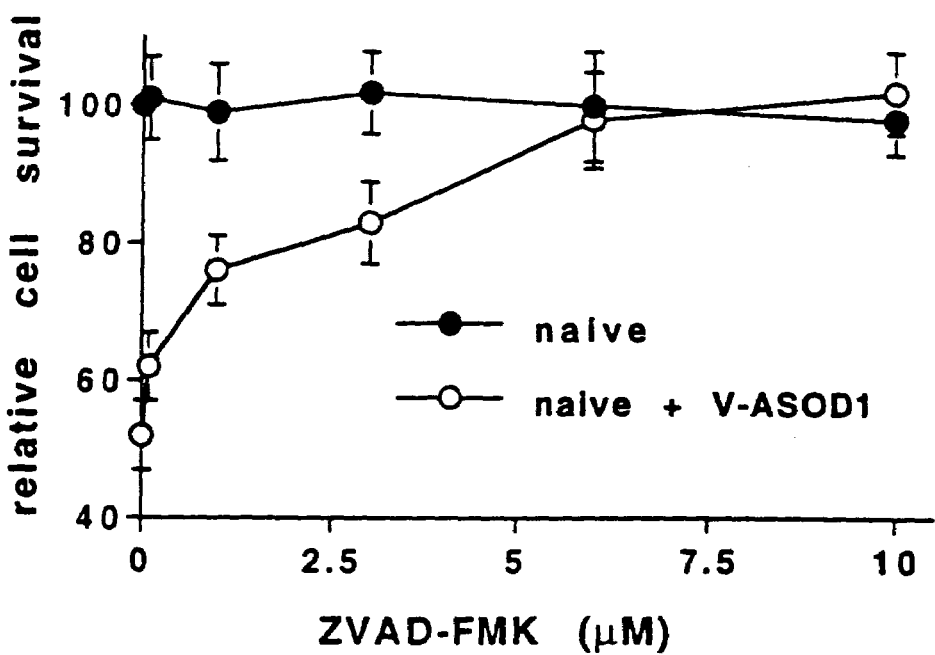

FIGS. 4A and 4B. V-ICE$_{inh}$ protects PC12 cells from death induced by down-regulation of SOD1. (A) Naive PC12 cells were washed and plated in RPMI 1640 medium with 10% horse serum and 5% fetal calf serum and incubated with or without V-ASOD1 (vector linked antisense oligonucleotide to superoxide dismutase) (50 nM) and the indicated concentrations of V-ICE$_{inh}$. Primed PC12 cells (PC12 cells treated with NGF for more than 7 days) were washed and replated in RPMI 1640 medium supplemented with 1% horse serum and NGF (100 ng/ml), and incubated with or without V-ASOD1 (50 nM) and the indicated concentrations of V-ICE$_{inh}$. Quantification of surviving cells was at one day. (B) ZVAD-FMK (Seq. I.D. No. 2) protects PC12 cells from V-ASOD1 induced death. Naive PC12 cells were treated as in FIG. 4A, incubated with V-ASOD1 (50 nM) together with the indicated concentrations of ZVAD-FMK (Seq. I.D. No. 2) and quantified at one day for proportion of surviving cells.

FIGS. 5A, 5B, 5C and 5D. Blockade of IL-1β protects from neurotrophin-deprivation induced and from SOD1 down-regulation-induced death. (A) IL-1β antibody protects from SOD1 down-regulation but not from trophic deprivation. For V-ASOD1 experiments, PC12 cells were replated as described in FIG. 4, with and without IL-1β antibody. For trophic deprivation, PC12 cells were extensively washed and plated as described in FIG. 2 in serum-free RPMI, with and without the IL-1β antibody. Quantification of surviving cells was at one day. V-ASOD1 treated cells had 47% survival, control cells received serum. Serum deprived cells had 48% survival, control cells received NGF. Data are reported as the percentage increase in surviving cells. (B) IL-1ra protects PC12 cells from SOD1 down-regulation completely and from trophic deprivation partially. PC12 cells were plated as described in FIG. 5A, with and without IL-1ra. Quantification of surviving cells was at one day. V-ASOD1-treated cells had 47% survival, serum-deprived cells had 26% survival. Data are reported as the percentage increase in surviving cells. (C) IL-1β levels are increased by NGF treatment or by V-ASOD1 treatment. PC12 cells were plated as described in FIGS. 2 and 4, with and without V-ICE$_{inh}$ (200 μM for trophic deprivation, 25 nM for V-ASOD1 treatment). After 20 hours, media was removed and IL-1β measured by ELISA. Surviving cells were quantified at 20 hrs. (D) IL-1β potentiates V-ASOD1 induced death. PC12 cells were plated as described in FIG. 4, with the indicated additives: IL-1β at 1 μg/ml, V-ASOD1 at 50 nM, and V-ICE$_{inh}$ at 25 nM.

DETAILED DESCRIPTION OF THE INVENTION

The present invention provides for a compound having the structure: $(AA_1)_n$-Cys-$(AA_2)_m$ wherein n=0,1,2,3,4 or 5 and m=0,1,2,3,4 or 5, provided the sum of (n+m) is greater than or equal to two and less than or equal to five, if n=1, $(AA_1)_n$=Ala-, if n=2, $(AA_1)_n$=Gln-Ala-, if n≧3, $(AA_1)_n$=$(Xaa)_p$-Gln-Ala-,and Xaa=any amino acid and wherein if n=3, p=1, if n=4, p=2, if n=5, p=3, if m=1, $(AA_2)_m$=-Arg, if m=2, $(AA_2)_m$=-Arg-Gly, if m≧3, $(AA_2)_m$=-Arg-Gly-$(Xaa)_q$, wherein if m=3, q=1, if m=4, q=2, if m=5, q=3.

The present invention also provides for a compound having the structure: $(AA_1)_n$-Cys-$(AA_2)_m$ wherein n=0,1,2 or 3 and m=0,1,2 or 3, provided the sum of (n+m) is greater than or equal to two and less than or equal to five, if n=1, $(AA_1)_n$=Ala-, if n=2, $(AA_1)_n$=Gln-Ala-, if n=3, $(AA_1)_n$=$(Xaa)_p$-Gln-Ala-,and Xaa=any amino acid and wherein if n=3, p=1, if m=1, $(AA_2)_m$=-Arg, if m=2, $(AA_2)_m$=-Arg-Gly, if m=3, $(AA_2)_m$=-Arg-Gly-$(Xaa)_q$, wherein if m=3, q=1.

The present invention also provides for a compound having the structure: $(AA_1)_n$-Cys-$(AA_2)_m$ wherein n=2 or 3 and m=0,1,2 or 3, provided the sum of (n+m) is greater than or equal to two and less than or equal to five, if n=2, $(AA_1)_n$=Gln-Ala-, if n=3, $(AA_1)_n$=$(Xaa)_p$-Gln-Ala-, and Xaa=any amino acid and wherein if n=3, p=1, if m=1, $(AA_2)_m$=-Arg, if m=2, $(AA_2)_m$=-Arg-Gly, if m=3, $(AA_2)_m$=-Arg-Gly-$(Xaa)_q$, wherein if m=3, q=1.

The compound may be Ile-Gln-Ala-Cys-Arg-Gly (Seq. I.D. No. 1) or Gln-Ala-Cys-Arg-Gly (Seq. I.D. No. 3).

The present invention also provides for a compound having the structure:

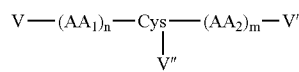

wherein n, m, $(AA_1)_n$ and $(AA_2)_m$ are as described above. In the compound each V, V' or V" is independently an agent capable of specifically directing the compound to a cell. V, V' or V" may be a polypeptide including at least a portion of an Antennepedia polypeptide. V, V' or V" may be at least a portion of a polypeptide including the sequence NPyS-Arg-Gln-Ile-Lys-Ile-Trp-Phe-Gln-Asn-Arg-Arg-Met-Lys-Trp-Lys-Lys-(Seq. I.D. No. 9). The compound may be NPyS-Arg-Gln-Ile-Lys-Ile-Trp-Phe-Gln-Asn-Arg-Arg-Met-Lys-Trp-Lys-Lys-Ile-Gln-Ala-Cys-Arg-Gly (Seq. I.D. No. 10). The compound may be NPyS-Arg-Gln-Ile-Lys-Ile-Trp-Phe-Gln-Asn-Arg-Arg-Met-Lys-Trp-Lys-Lys-Gln-Ala-Cys-Arg-Gly (Seq. I.D. No. 11). V, V' or V" may be independently an antibody, an adjuvant or a cell-specific ligand. The cell may be a neuronal cell, a cardiac cell or a liver cell.

The peptidomimetic compound may be at least partially unnatural. The peptidomimetic compound may be a small molecule mimic of Ile-Gln-Ala-Cys-Arg-Gly or of Gln-Ala-Cys-Arg-Gly. The compound may have increased stability, efficacy, potency and bioavailability by virtue of the mimic. Further, the compound may have decreased toxicity. The peptidomimetic compound may have enhanced mucosal intestinal permeability. The compound may be synthetically prepared. The compound of the present invention may include L-,D- or unnatural amino acids, alpha, alpha-disubstituted amino acids, N-alkyl amino acids, lactic acid (an isoelectronic analog of alanine). The peptide backbone of the compound may have at least one bond replaced with PSI-[CH=CH] (Kempf et al. 1991). The compound may further include trifluorotyrosine, p-Cl-phenylalanine, p-Br-phenylalanine, poly-L-propargylglycine, poly-D,L-allyl glycine, or poly-L-allyl glycine.

One embodiment of the present invention is a peptidomimetic compound having the biological activity of the structure: $(AA_1)_n$-Cys-$(AA_2)_m$ as described above wherein the compound has a bond, a peptide backbone or an amino acid component replaced with a suitable mimic. Examples of unnatural amino acids which may be suitable amino acid mimics include β-alanine, L-α-amino butyric acid, L-γ-amino butyric acid, L-α-amino isobutyric acid, L-ε-amino caproic acid, 7-amino heptanoic acid, L-aspartic acid, L-glutamic acid, cysteine (acetamindomethyl), N-ε-Boc-N-α-CBZ-L-lysine, N-ε-Boc-N-α-Fmoc-L-lysine, L-methionine sulfone, L-norleucine, L-norvaline, N-α-Boc-N-δCBZ-L-ornithine, N-δ-Boc-N-α-CBZ-L-ornithine, Boc-p-nitro-L-phenylalanine, Boc-hydroxyproline, Boc-L-thioproline. (Blondelle, et al. 1994; Pinilla, et al. 1995).

Another embodiment of the present invention is a pharmaceutical composition including an amount of a compound having the structure: $(AA_1)_n$-Cys-$(AA_2)_m$ or

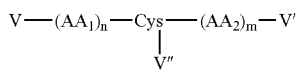

as described above effective to inhibit the death of a cell and a pharmaceutically acceptable carrier thereof. The cell may be a neuronal cell, a cardiac cell or a liver or a hepatic cell. The carrier may include a diluent. The carrier may include an appropriate adjuvant, a herpes virus, a liposome, a microencapsule, a neuronal cell receptor ligand, a neuronal-specific virus, a polymer encapsulated cell or a retroviral vector. The pharmaceutically acceptable carrier may include an aerosol, intravenous, oral or topical carrier.

Another embodiment of the present invention is a method of inhibiting death of a cell which includes contacting the cell with an amount of a compound having the structure:

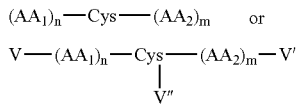

effective to inhibit death of the cell. The cell may be in a subject. The subject may be a human. The cell may be a neuronal cell, a cardiac cell or a hepatic cell.

Another embodiment of the present invention is a method for alleviating symptoms of a neurodegenerative disorder in a subject which includes administering to the subject the compounds described hereinabove, the compound being present in an amount effective to inhibit neuronal cell death and thus alleviate the symptoms of the neurodegenerative disorder in the subject.

The neurodegenerative disorder may be associated with aging, Alzheimer's disease, dentatorubral and pallidolyusian atrophy, Huntington's disease, Machoado-Joseph disease, multiple sclerosis, muscular dystrophy, Parkinson's disease, senility, spinocerebellar ataxia type I, spinobulbar muscular atrophy, stroke, trauma. The subject may be a mammal. The mammal may be a human. The administration may include aerosol delivery; intralesional, intraperitoneal, intramuscular or intravenous injection; infusion; liposome-mediated delivery; anal, nasal, oral, ocular, otic or topical delivery of the pharmaceutical composition.

The present invention also provides for a method for alleviating symptoms of a cardiovascular disorder in a subject which includes administering to a subject either of the compounds described hereinabove, the compound being present in an amount effective to inhibit cardiac cell death and thus alleviate the symptoms of the cardiovascular disorder in the subject.

The present invention also provides for a method of alleviating symptoms of a liver disorder in a subject which includes administering to the subject either of the compounds described hereinabove, the compound being present in an amount effective to inhibit liver cell death and thus, alleviate the symptoms of the liver disorder in the subject.

Previously, researchers have searched for an inhibitor of ICE which is capable of acting as a psuedosubstrate as discussed above. This invention provides an unusual approach to the problem of inhibiting the ICE enzyme. The present invention provides for compounds which are capable of inhibiting cell death. These compounds may be capable of inhibiting ICE and preventing cell death. Specifically, the compounds may be capable of preventing neuronal cell death, cardiac cell death or hepatic (liver) cell death.

The effectiveness of the compounds described herein as an enzyme inhibitor to prevent cell death is a surprising result that would not have been anticipated by one skilled in the art. The conventional approach to developing an inhibitor of an enzyme is to mimic the substrate of that enzyme. The non-active substrate mimic is usually designed to bind to the active site of the enzyme to be inhibited. This binding is usually at a higher affinity than the normal substrate. Thus, while the active site of the enzyme is bound to the mimic, it is non-productive and not active. Design of a compound which is capable of occupying the active site of an enzyme and competing with the normal substrate for binding is the classic approach to enzyme inhibition. The present invention, however, provides for an alternate approach to this problem utilizing a portion of the enzyme itself.

Also provided by the invention are pharmaceutical compositions comprising therapeutically effective amounts of polypeptide products of the invention together with suitable diluents, preservatives, solubilizers, emulsifiers, adjuvants and/or carriers. A "therapeutically effective amount" as used herein refers to that amount which provides a therapeutic effect for a given condition and administration regimen. Such compositions are liquids or lyophilized or otherwise dried formulations and include diluents of various buffer content (e.g., Tris-HCl., acetate, phosphate), pH and ionic strength, additives such as albumin or gelatin to prevent absorption to surfaces, detergents (e.g., Tween 20, Tween 80, Pluronic F68, bile acid salts), solubilizing agents (e.g., glycerol, polyethylene glycerol), anti-oxidants (e.g., ascorbic acid, sodium metabisulfite), preservatives (e.g., Thimerosal, benzyl alcohol, parabens), bulking substances or tonicity modifiers (e.g., lactose, mannitol), covalent attachment of polymers such as polyethylene glycol to the protein, complexation with metal ions, or incorporation of the material into or onto particulate preparations of polymeric compounds such as polylactic acid, polyglycolic acid, hydrogels, etc, or onto liposomes, microemulsions, micelles, unilamellar or multilamellar vesicles, erythrocyte ghosts, or spheroplasts. Such compositions will influence the physical state, solubility, stability, rate of in vivo release, and rate of in vivo clearance. The choice of compositions will depend on the physical and chemical properties of the protein having the activity of inhibiting neuronal cell death. For example, a product derived from a membrane-bound form of the protein may require a formulation containing detergent. Controlled or sustained release compositions include formulation in lipophilic depots (e.g., fatty acids, waxes, oils). Also comprehended by the invention are particulate compositions coated with polymers (e.g., poloxamers or poloxamines) and the compound coupled to antibodies directed against tissue-specific receptors, ligands or antigens or coupled to ligands of tissue-specific receptors. Other embodiments of the compositions of the invention incorporate particulate forms protective coatings, protease inhibitors or permeation enhancers for various routes of administration, including parenteral, pulmonary, nasal, oral, injection or infusion by intravenous, intraperitoneal, intracerebral, intramuscular, intraocular, intraarterial or intralesional.

The present invention incorporates U.S. Pat. Nos. 5,446,128, 5,422,426 and 5,440,013 in their entireties as references which disclose the synthesis of peptidomimetic compounds and methods related thereto. The compounds of the present invention may be synthesized using these methods. The present invention provides for peptidomimetic compounds which have substantially the same three-dimensional structure as those peptide compounds described herein (Ojala et al., 1995; Bock et al., 1992; Lee et al., 1995).

In addition to the compounds disclosed herein having naturally-occurring amino acids with peptide or unnatural linkages, the present invention also provides for other structurally similar compounds such as polypeptide analogs with unnatural amino acids in the compound. Such compounds may be readily synthesized on a peptide synthesizer available from vendors such as Applied Biosystems, Dupont and Millipore.

The present invention includes a delivery system which links the polypeptide to an agent which directs the polypeptide to neuronal cells in order to facilitate entry into the cells. The Antennepedia protein may be used as such a delivery agent. The invention also includes therapeutic uses of the isolated polypeptide to prevent neuronal cell death, cardiac cell death or hepatic cell death. Related therapeutic uses include treating stroke, trauma, neurodegenerative disorders or regenerating neurons, cardiac ischemia, liver disease, pulmonary disease, congestive heart disease, myocardial infarction, Alzheimer's disease, Parkinson's disease, senility, aging, muscular dystrophy, multiple sclerosis, Huntington's disease, spinocerebellar ataxia type I, Machoado-Joseph disease, spinobulbar muscular atrophy or dentatorubral and pallidolyusian atrophy.

The present invention provides for a method of identifying a peptide compound as an enzyme inhibitor which includes preparing suitable peptide fragments chosen from an active site of an enzyme, assaying the fragments and identifying the fragments which are enzyme inhibitors. The present invention also encompasses a compound obtained by this method. The enzyme may include a protein kinase enzyme, an enzyme associated with cellular signaling, an enzyme associated with cell death, or a bcl-2 enzyme. The enzyme may also include an enzyme associated with cellular communication, cell division, cellular metabolism, cell adhesion, gene expression or protein processing. (Adams M. D. et al., 1995)

The present invention also provides for a method of inhibiting the activity of an enzyme on a substrate which includes contacting the enzyme with a peptide fragment or a peptidomimetic fragment from an active site of the enzyme under conditions that the fragment is capable of binding to the substrate of the enzyme and thus inhibiting the activity of the enzyme on the substrate.

Another embodiment of the present invention is a method of inhibiting the activity of an enzyme on a substrate in a cell which includes contacting the enzyme with a peptide fragment or a peptidomimetic fragment from an active site of the enzyme under conditions that the fragment is capable of binding to the substrate of the enzyme and thus inhibiting the activity of the enzyme on the substrate.

This invention is illustrated in the Experimental Detail section which follows. These sections are set forth to aid in an understanding of the invention but are not intended to, and should not be construed to, limit in any way the invention as set forth in the claims which follow thereafter.

Experimental Details

EXAMPLE 1

The Contrasting Roles of ICE-family Proteases and Interleukin-1β in Apoptosis Induced by Trophic Factor Withdrawal and by SOD1 Down-regulation Previous results have shown that down-regulation of $Cu^{++}$-$Zn^{++}$ superoxide dismutase (SODL) in PC12 cells produces apoptosis by mechanisms that are distinguishable upstream from those utilized by trophic factor deprivation (Troy and Shelanski, 1994) but which may converge downstream in a final common pathway. To determine whether the ICE (interleukin 1β converting enzyme) family of proteases is required for apoptosis induced by oxidative stress as well as by trophic factor withdrawal, a novel Antennapedia-linked peptide inhibitor was developed that mimics the common catalytic site of these enzymes and thereby blocks their access to substrates, a unique approach to enzyme inhibition. Blockade of ICE family proteases by this inhibitor as well as by a permeant competitive antagonist, rescues PC12 cells from apoptotic death following trophic factor/NGF-deprivation as well as from peroxynitrite-dependent apoptosis induced by down-regulation of SOD1. In spite of the protection afforded by ICE family inhibitors in these two paradigms, blocking antibodies to IL-1β and the IL-1 receptor antagonist (IL-Ra) were fully protective only in the case of SOD1 down-regulation. The blocking antibody failed to protect PC12 cells from trophic factor withdrawal and the receptor antagonist was only partially protective at very high concentrations. Similarly, there were substantial differences in the concentrations of pseudo substrate inhibitors which rescued cells from SOD1 down-regulation and trophic factor deprivation. These results suggest the involvement of different members of the ICE family, different substrates or both in the two different initiating causes of cell death.

Introduction

Oxidative damage is a major contributor to cell death in a variety of degenerative disorders (Coyle and Puttfarcken, 1993). In model systems, it appears to be initiated by mechanisms that are distinguishable from apoptosis brought about by serum or trophic factor withdrawal (Troy and Shelanski, 1994). In the clonal rat pheochromocytoma line PC12, a commonly used model for neuronal differentiation and cell death (Greene and Tischler, 1976; Rukenstein et al., 1991; Ferrari et al., 1995; Pittman et al., 1993; and Ferrari and Greene, 1994), both trophic factor withdrawal and down-regulation of $Cu^{++}$-$Zn^{++}$ superoxide dismutase (SOD1) result in apoptosis (Troy and Shelanski, 1994 and Batistatou and Greene, 1991). The former, trophic factor withdrawal, is inhibited by cAMP analogues (Rukenstein et al., 1991), N-acetylcysteine (Ferrari et al., 1995) and a variety of growth factors including NGF (Rukenstein et al., 1991 and Pittman et al., 1993), but not by vitamin E (Ferrari et al., 1995) or inhibitors of nitric oxide synthase (Farinelli et al., 1995), and appears to be related to an abortive attempt to traverse the cell cycle (Ferrari and Greene, 1994). The latter, SOD1 down regulation, in contrast, is insensitive to cAMP analogs, N-acetylcysteine and growth factors, but is blocked by vitamin E and, consistent with a role for peroxynitrite generation, by nitric oxide synthase inhibitors (Troy and Shelanski, 1994). Despite these divergent initial causes of death, it has been shown that bcl-2 overexpression rescues PC12 cells from death induced by either trophic factor deprivation (Batistatou et al., 1993) or SOD1 down-regulation indicating that the apoptotic pathways ultimately converge. Inhibition of ICE-like proteases has also been shown to block apoptosis induced by trophic factor deprivation but the role of these enzymes in oxygen-radical induced death has not been previously explored. The studies presented here show an obligate role for ICE-like proteases in both paradigms and place them, together with bcl-2, on the shared branch of the apoptotic pathway. However, these studies also show that IL-1β itself can play a critical role in death initiated by SOD1 down-regulation, but only a minor role in apoptosis caused by withdrawal of trophic support and therefore suggest involvement of different members of the ICE family in the two initiating causes of cell death.

Materials and Methods

Cell Culture of PC12 cells: PC12 cells were grown as previously described (Greene and Tishcler, 1976) on rat-tail collagen-coated dishes in RPMI 1640 medium containing 5% fetal calf serum and 10% heat-inactivated horse serum (complete medium). NGF primed PC12 cells were grown for at least 7 days in RPMI 1640 medium plus 1% horse serum and NGF (100 ng/ml). For cell survival assays involving trophic factor deprivation, cells (either naive or NGF-pretreated) were extensively washed in serum-free RPMI 1640 medium and re-plated on fresh collagen-coated 24-well dishes as previously described (Rukenstein et al., 1991) in RPMI 1640 medium lacking serum or NGF. For SOD1 down-regulation survival assays, cells were re-plated in complete medium with V-ASOD1 (vector linked antisense oligonucleotide to SOD1, 50 nM). Various concentrations of ICE inhibitors were included in the medium as indicated. Numbers of viable cells per culture were determined by quantifying intact nuclei as previously described (Rukenstein et al., 1991). Counts were performed in triplicate and reported as means±SEM.

Cell Culture of Sympathetic neurons: Sympathetic neuron cultures were prepared from 2 day old rat pups, as previously described (Ferrari et al., 1995). Cultures were grown in 24-well collagen coated dishes in RPMI 1640 medium plus 10% horse serum with mouse NGF (100 ng/ml). One day following plating, uridine and 5-fluorodeoxyuridine (10 μM each) were added to the cultures and left for three days to eliminate non-neuronal cells. On the sixth day following plating NGF was removed by washing the cultures three times with RPMI 1640 medium plus 10% horse serum, followed by the addition of medium containing anti-mouse NGF (1:200, Sigma) with or without ICE inhibitors. Each culture was scored, as previously described (Rydel and Greene, 1988), as numbers of living, phase-bright neurons at various times. Three replicate cultures were assessed for each condition and data were normalized to numbers of neurons present in each culture at the time of NGF withdrawal and reported as mean±SEM.

Assay of ICE activity: Recombinant human pro-IL-1β was purchased from Cistron Biotechnology (Pine Brook, N.J.) as a 10 μg ml$^{-1}$ solution in 10 mM Tris (pH 8.1), 0.1% Triton X-100, 0.1 mM EDTA and 10% glycerol. The assay of pro-IL-1β cleavage was carried out in buffer containing 100 mM HEPES (pH 7.5), 0.1% CHAPS, 10 mM DTT and 10% sucrose. 10 ng of pro-IL-1-B was incubated with or without 1 mM IQACRG (Seq. I.D. No. 1) for 30 minutes at 37° C. 3 units of recombinant human ICE were then added and the reaction mixtures were incubated for 30 minutes at 25° C. (Thornberry, 1994). Reactions were stopped with 2× Laemmli sample buffer (Laemmli, 1970) containing 10 mM DTT and the samples were boiled for 3 minutes and subjected to SDS-PAGE (15% acrylamide) followed by immunoblotting. The blot was probed with a monoclonal antibody to human IL-1β (0.25 μg/ml, kindly provided by the National Cancer Institute), and then visualized by ECL using anti-mouse IgG peroxidase as secondary antibody.

Coupling of Antennapedia peptide (vector peptide) with the hexapeptide IQACRG (Seq. I.D. No. 1)—ICE family inhibitor: IQACRG (Seq. I.D. No. 1)(synthesized by e.g., Multiple Peptide Systems (California), American Peptide Company (California), The Midland Certified Reagent Company (Texas)) was resuspended in TCEP (tris(2-carboxyethyl)-phosphine hydrochloride) buffer, an equimolar ratio of NPyS-pAntp$_{43-58}$ peptide (Penetratin 1, Oncor, Md.) hereafter called the vector peptide) was added and the mixture was incubated at 20° C. for 2 hours. The sequence of the vector peptide is NPyS-Arg-Gln-Ile-Lys-Ile-Trp-Phe-Gln-Asn-Arg-Arg-Met-Lys-Trp-Lys-Lys (Seq. I.D. No. 9). The yield of the reaction, estimated by SDS-PAGE followed by Coomasie blue staining, was routinely above 50%. Control peptides (GRCAQI (Seq. I.D. No. 4) and ICGRQA (Seq. I.D. No. 5) were coupled to the vectorpeptide in the same way.

Assay of IL-1β: IL-1β was quantified by ELISA using the Intertest-1βX kit (Genzyme, Cambridge, Mass.) . PC12 cells were grown as described above, on 24-well plates, in 500 μl of medium. After one day incubation, medium was removed and IL-1β measured following the manufacturer's instructions, and number of viable cells in each well quantified.

Additional Materials: ZVAD-FMK (Seq. I.D. No. 2) was from Enzyme Systems Products, Inc. (Dublin, Calif.) and ZYVAD-CMK (Seq. I.D. No. 6) from Bachem (King of Prussia, Pa.). Monoclonal human and murine IL-1β antibody (3ZD) was kindly provided by the NCI, as was recombinant human IL-1β. Blocking monoclonal hamster anti-mouse IL-1β was purchased from Genzyme, (Cambridge, Mass.), blocking anti-murine IL-1a from R&D Systems.

Results

In these studies, three paradigms were used to induce apoptosis in cultured PC12 cells. In the first, naive PC12 cells without NGF exposure are induced to die by the withdrawal of serum. In the second, PC12 cells which have been "primed" by NGF pretreatment in serum-free medium for a week and which have a neuronal morphology undergo apoptosis upon withdrawal of NGF and serum. The third model induces apoptosis by down-regulating superoxide dismutase 1 (SOD1) in either primed or naive cells by exposure to an SOD1 antisense oligonucleotide. Withdrawal of serum results in the death of 50–85% of the cells within 24 hours and NGF/serum deprivation and SOD1 down-regulation in 50–60% mortality by this time (Troy and Shelanski, 1994; Rukenstein et al., 1991; and Ferrari et al., 1995).

Figure 1A:
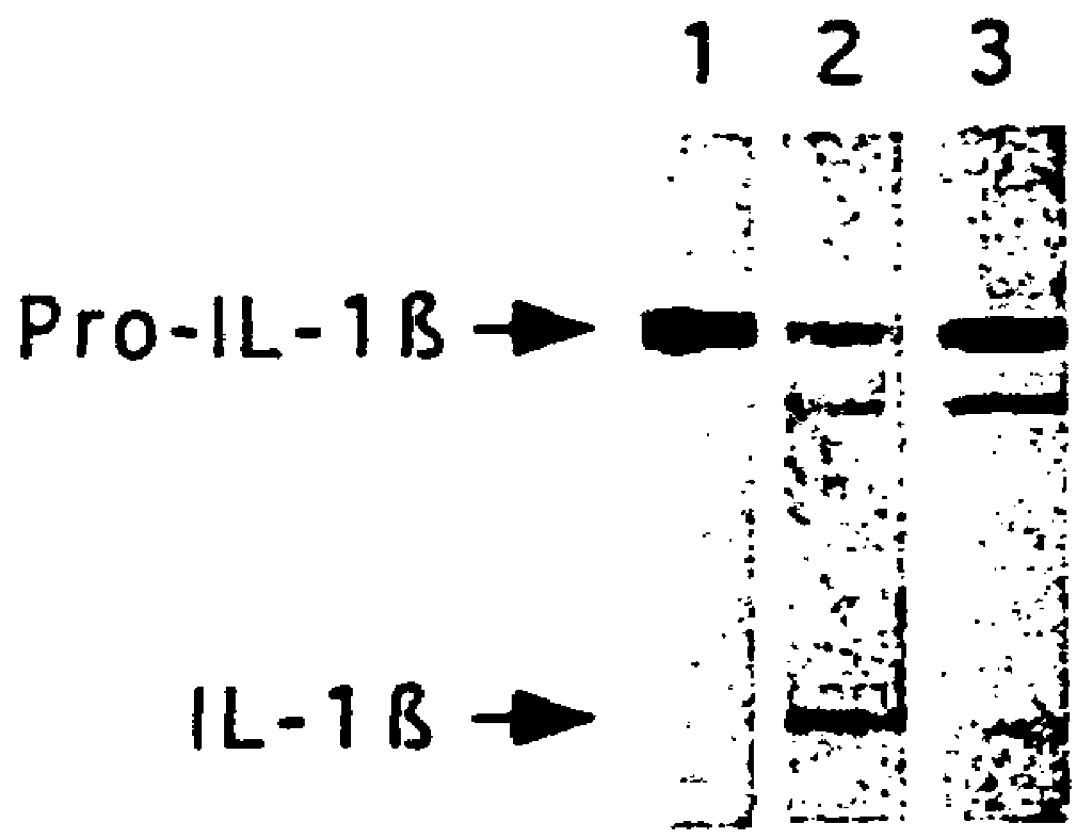
FIGS. 1A and 1B. (A) IQACRG (Seq. I.D. No. 1) blocks cleavage of pro-IL-1β by ICE. Enzyme digests were subjected to SDS-PAGE (15% acrylamide) followed by immunoblotting. The blot was probed with a monoclonal antibody to human and murine IL-1β (1 µg/ml), and then visualized by ECL using anti-mouse IgG peroxidase as a secondary antibody. Lane 1=pro-IL-1β, lane 2=pro-IL-1β+ICE, lane 3=pro-IL-1β+ICE+IQACRG (Seq. I.D. No. 1). (B) Schematic illustration of the coupling of Antennapedia peptide (vector peptide; hashed box) with the hexapaptide IQACRG (Seq. I.D. No. 1).
Figure 1B:
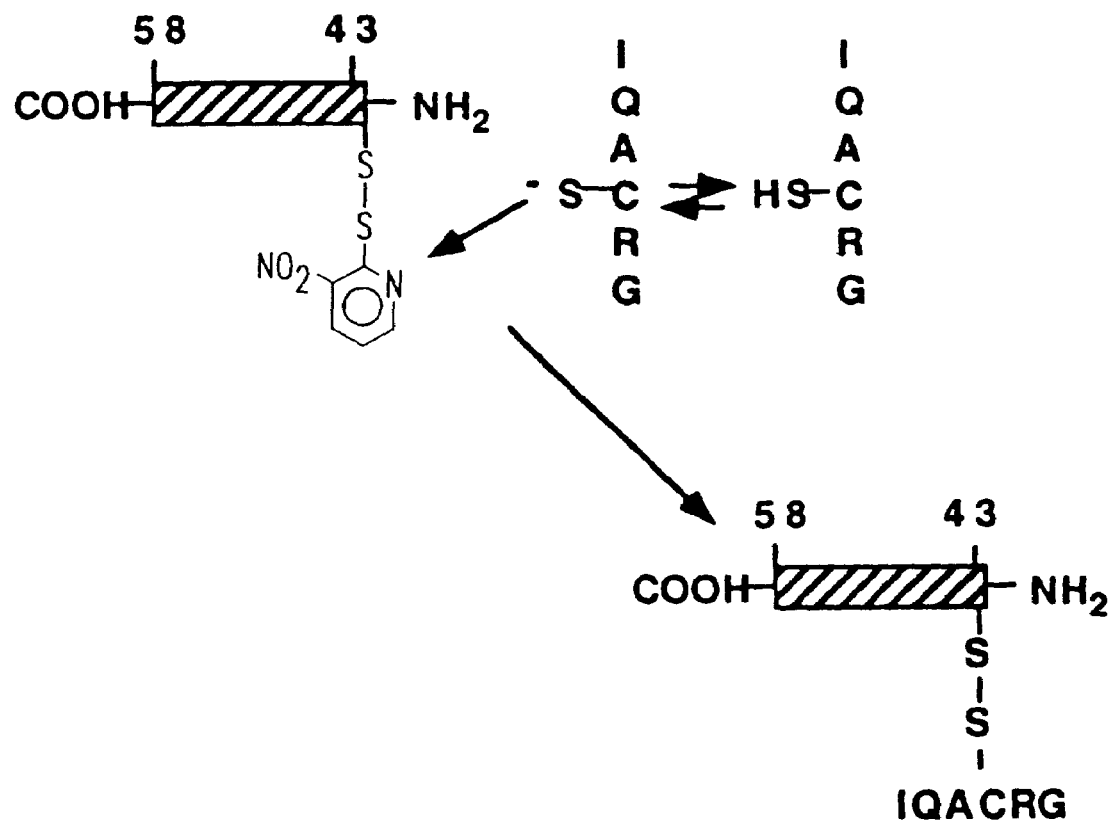

To investigate the role that ICE-like proteases play in apoptosis induced by these treatments, a peptide was utilized which mimics the conserved active site, IQACRG (Seq. I.D. No. 1), of the ICE-family of proteases (Wang et al., 1994) and which was anticipated to bind to substrates and thereby block their cleavage. IQACRG (Seq. I.D. No. 1) should inhibit activity regardless of the specific substrate, avoiding the problem posed by differences in the preferred substrate for individual members of the ICE family. A search of the Swiss Protein Bank revealed that only ICE family members have this sequence. This approach also minimizes the chance of blocking cysteine proteases other than those in the ICE-family. To verify that IQACRG (Seq. I.D. No. 1) blocks ICE activity, the capacity of recombinant ICE to cleave recombinant pro-IL-1β was tested in the presence or absence of the peptide. As shown in FIG. 1A, the peptide effectively inhibits. ICE cleavage of pro-IL-1β in vitro. There is some cleavage in the presence of the inhibitor but much less than seen with ICE alone. Cellular uptake of the IQACRG (Seq. I.D. No. 1) peptide was facilitated by linking it to the highly penetrant 16 amino acid Antennapedia peptide (FIG. 1B) which greatly enhances cellular uptake of peptides as well as antisense oligonucleotides (Prochiantz and Theodore, 1995). The Antennapedia vector peptide (V-) was linked to IQACRG (Seq. I.D. No. 1) ($ICE_{inh}$) by a reducible disulfide bond to form $V-ICE_{inh}$. Previous studies have shown that after uptake, reduction of the S—S bond releases free peptide within the cell.

Figure 2A:
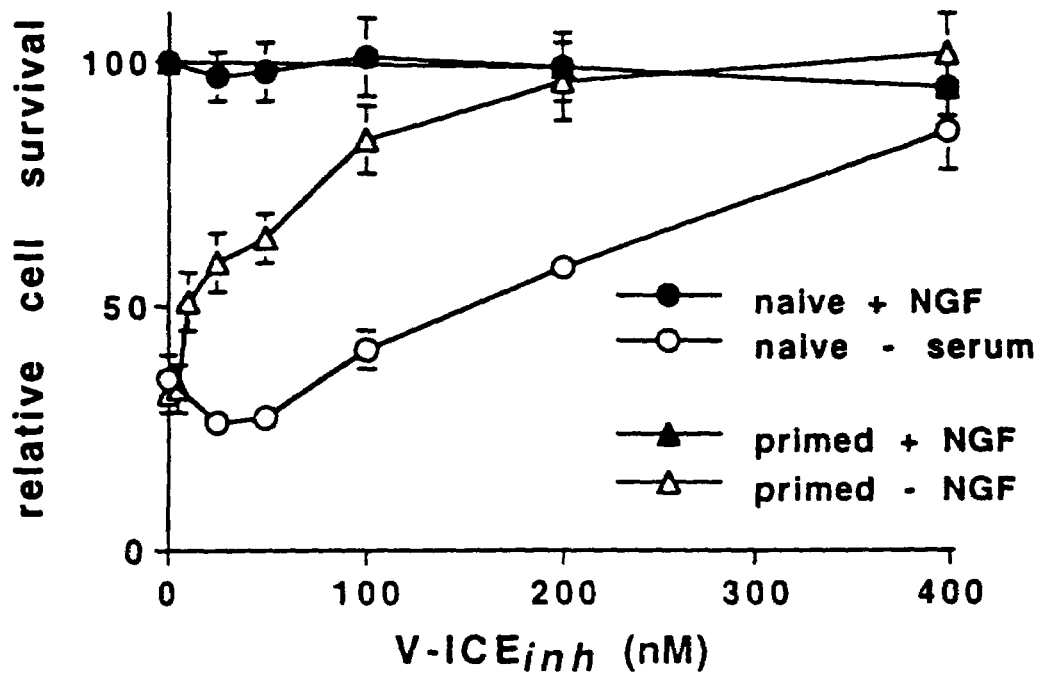
FIGS. 2A, 2B and 2C. V-ICE$_{inh}$ protects PC12 cells from death induced by withdrawal of serum/NGF. (A) Protection of PC12 cells from serum/trophic factor deprivation induced death. Naive and primed PC12 cells (PC12 cells treated with NGF for more than 7 days) were extensively washed and plated in serum-free RPMI 1640 with the indicated concentrations of V-ICE$_{inh}$. Control cultures received readditions of NGF. One day later, the numbers of surviving cells were determined by lysing the cultures and counting intact nuclei. Cell number is reported relative to those present in control cultures with NGF and without V-ICE$_{inh}$ (designated as 100). The numbers of cells in control cultures at 24 hrs were within 10% of those initially plated. (B) Time course of protection of NGF-deprived PC12 cells by V-ICE$_{inh}$. Primed PC12 cells were deprived of NGF as above and then maintained with or without V-ICE$_{inh}$ (200 nM) for the indicated times. V-ICE$_{inh}$ was added at time 0 (1 addition) or at time 0 and at 24 hours (2 additions), as indicated and quantifications of survival were made at the indicated times by lysing the cells and counting nuclei as described in (A). (C) ZVAD-FMK (Seq. I.D. No. 2) protects PC12 cells from withdrawal of trophic support. PC12 cells were washed free of serum as in FIG. 2A and plated in serum-free medium with the indicated concentrations of ZVAD-FMK (Seq. I.D. No. 2) (ZVAD-fluoromethylketone, Enzyme Systems Products, Dublin, Calif.). Control cultures received NGF. At one day of incubation cells were lysed and surviving numbers determined as in FIG. 2A.
Figure 2B:
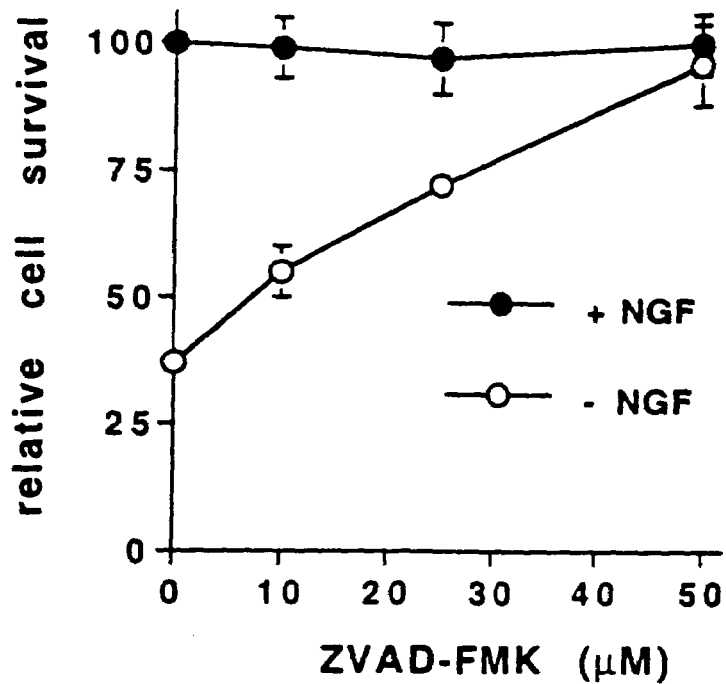
Figure 2C:
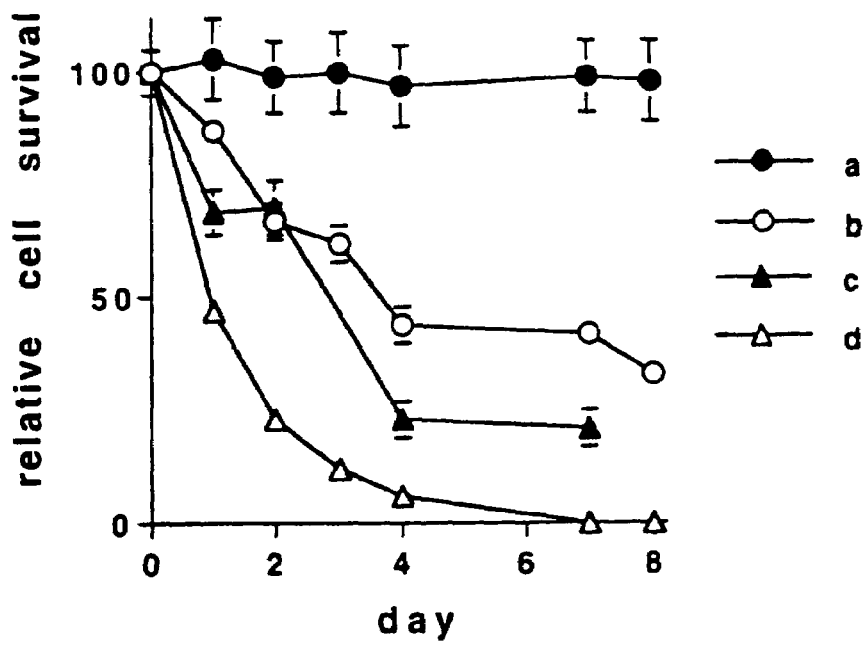

Inhibitors of ICE-like proteases protect PC12 cells and sympathetic neurons from death induced by withdrawal of serum and NGF. From the reported inhibition of cell death in NGF-deprived sensory neurons by crmA (Gagliardini et al., 1994), it was possible that if $V-ICE_{inh}$ significantly inhibits ICE-family proteases in vivo, it should block cell death caused by withdrawal of serum from naive PC12 cells and serum and NGF from neuronally-differentiated PC12 cells. The data in FIG. 2A show that this is the case with complete protection at 24 hours obtained with 200–400 nM peptide. Treatment with $V-ICE_{inh}$ provided partial protection of naive and primed PC12 cells (FIG. 2C) for at least 8 days. To control for possible non-specific actions of $V-ICE_{inh}$, reversed and scrambled V-linked peptides were also tested in the PC12 cell system and neither was found to be effective or toxic over the same concentration range. To further explore the role of ICE proteases in this system, the permeant competitive inhibitor ZVAD-FMK (Seq I.D. No. 2) (ZVAD-fluoromethylketone) was also assessed. This also blocked cell death, but required much higher concentrations (50 μM) to be fully protective (FIG. 2B). The peptide ZYVAD-CMK (Seq. I.D. No. 6) (ZYVAD-chloromethylketone) (Lazebnik et al., 1994), an additional competitive inhibitor of ICE family proteases, was only partially effective at 250 μM.

Figure 3A:
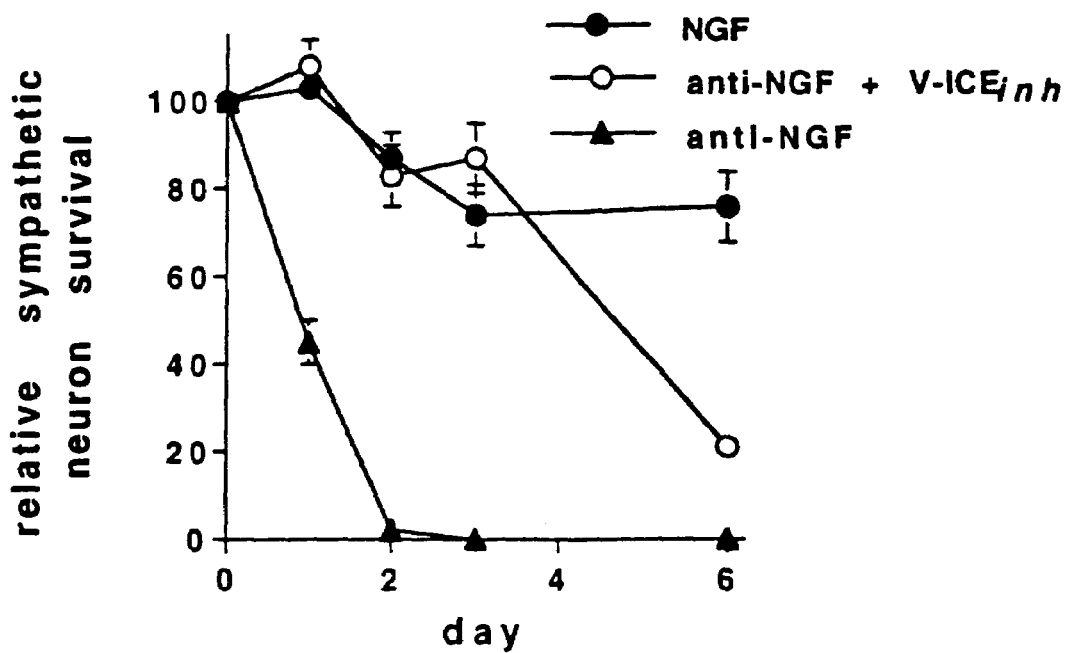
Figure 3B:
Figure 3C:
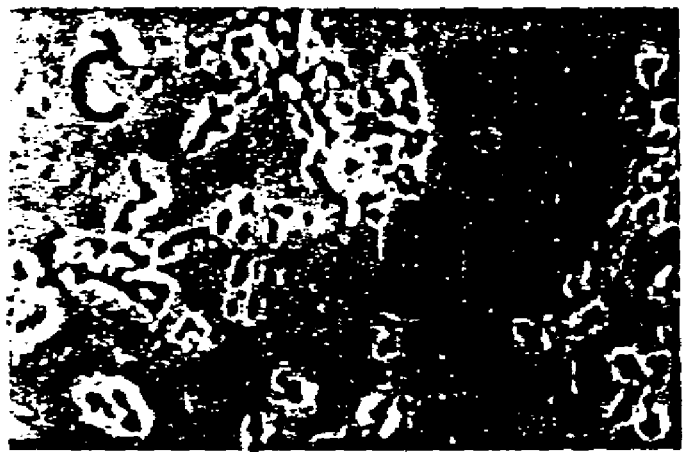
Figure 3D:

In parallel experiments, NGF-deprived sympathetic neurons exposed to $V-ICE_{inh}$ (50 nM) were completely protected from death for 3 days and death was retarded for at least 6 days (FIG. 3A). Although a second addition of $V-ICE_{inh}$ after 24 hr somewhat prolonged survival time, subsequent treatment at daily intervals did not. As reported with crmA protection (Gagliardini et al., 1994), cell bodies but not neurites are maintained with $V-ICE_{inh}$ (FIG. 3B–D). ZVAD-FMK (Seq. I.D. No. 2) (100 μM) also protected from NGF deprivation, but ZYVAD-CMK (Seq. I.D. No. 9) had no effect even at 250 μM.

$V-ICE_{inh}$ protects PC12 cells from death induced by down-regulation of SOD1. Exposure of PC12 cell cultures to the antisense oligonucleotide ASOD1 results in rapid down-regulation of SOD1 activity and death of 50–60% of the cells within 24 hr (Troy and Shelanski, 1994). As shown in FIG. 4A, $V-ICE_{inh}$ protects both naive and NGF-treated PC12 cells from death in this paradigm. Control, scrambled and reversed V-linked peptides were, in contrast, without effect. $V-ICE_{inh}$ had no effect on the capacity of ASOD1 to lower cellular SOD1. Protection was the same whether the experiment was done in complete medium or in RPMI 1640 supplemented with 3 μM insulin. The protective effects of inhibiting ICE-family proteases were confirmed using the inhibitory ZVAD-FMK (Seq. I.D. No. 2) peptide (FIG. 4B).

The dose of $V-ICE_{inh}$ (25–50 nM) required for maximal protection was again considerably lower than that for ZVAD-FMK (6 μM) (Seq. I.D. No. 2). However, the concentration of either required to protect cells from SOD1 down-regulation were significantly lower that those needed to block apoptosis caused by trophic factor withdrawal (compare FIGS. 2A and 4A). Moreover, ZYVAD-CMK (Seq. I.D. No. 9) afforded full protection from SOD1 down-regulation at 50 μM, in contrast to its partial protection from trophic factor withdrawal at 250 μM.

Figure 5A:
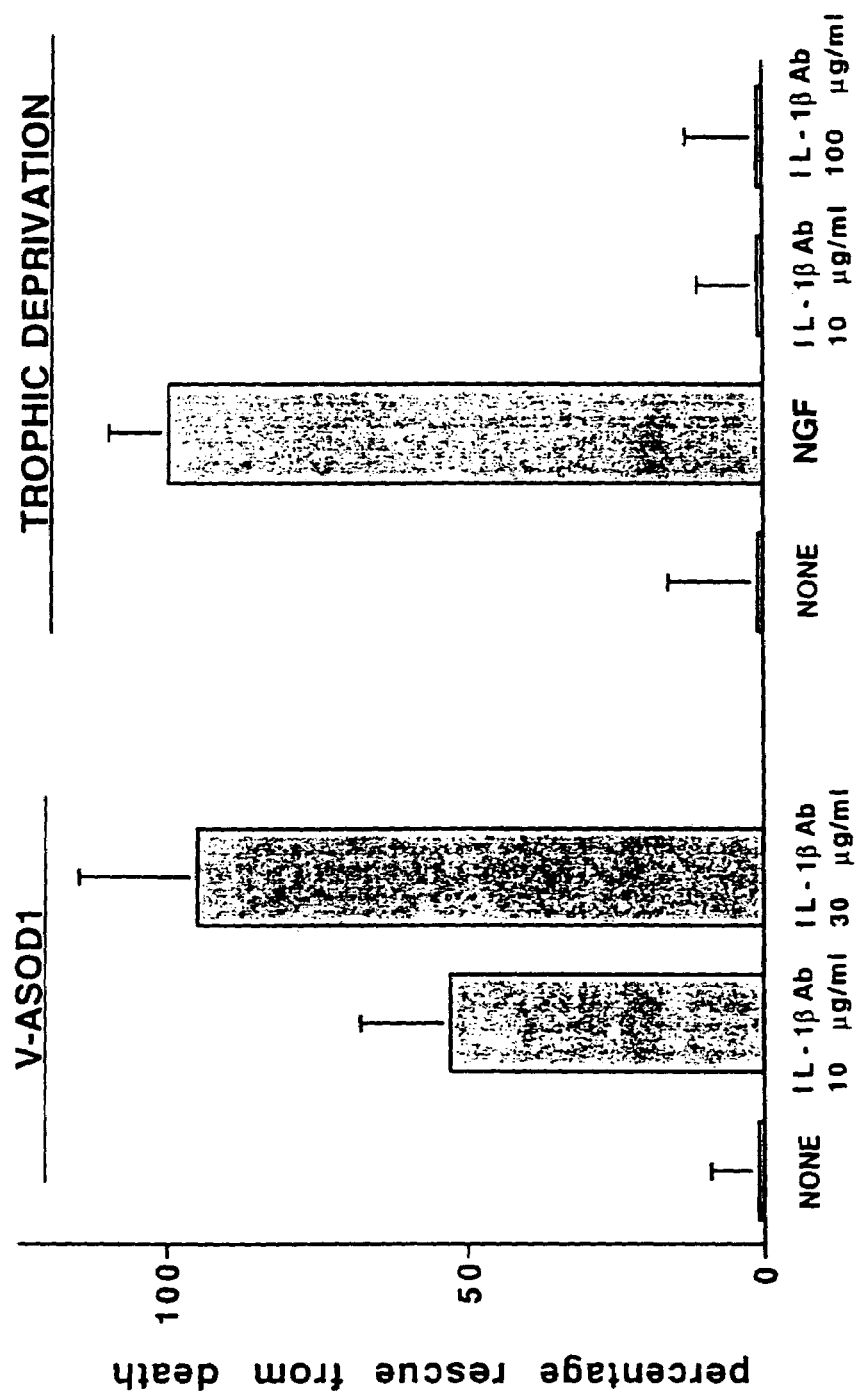
Figure 5B:
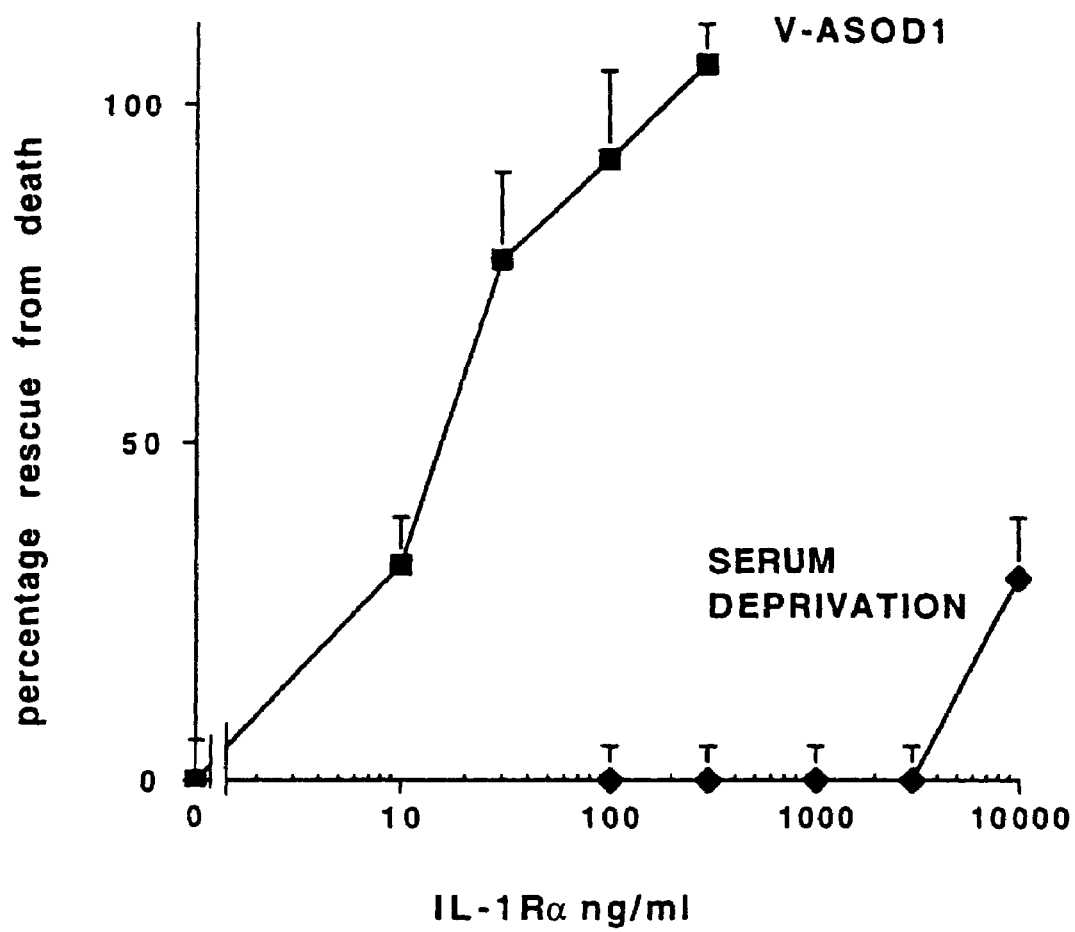

Both antibodies against IL-1β and an IL-1 receptor antagonist protect fully against SOD1 down-regulation but not trophic factor withdrawal. The inhibition of apoptosis by ICE inhibitors in each of the paradigms raised the question of whether IL-1β itself plays a direct role in cell death. Exposure of V-ASOD1 treated (SOD1 deficient) PC12 cells to blocking antibodies against mIL-1β at 30 μg/ml (FIG. 5A) or to the IL-1 receptor antagonist (rmIL-1Ra) at 100 ng/ml (FIG. 5B) completely suppressed cell death. Similar concentrations of antibodies against mIL-1a and a non-blocking antibody to mIL-1β failed to confer protection under these conditions. In contrast to the results in cells in which SOD1 had been down-regulated, the mIL-1β blocking antibody failed to protect cells from trophic factor withdrawal at concentrations up to 100 μg/ml (FIG. 5A). Furthermore, the IL-1 receptor antagonist improved survival under these conditions only modestly and then only at a concentration of 10,000 ng/ml (FIG. 5B), two orders of magnitude greater than the dose which fully protected cells from SOD1 down-regulation.

Figure 5C:
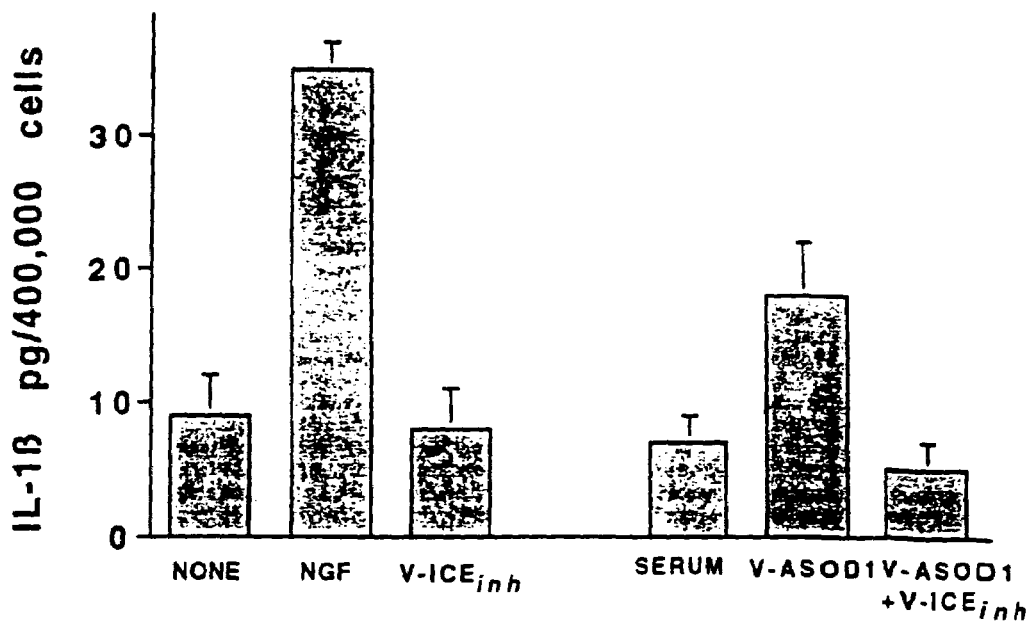
Figure 5D:
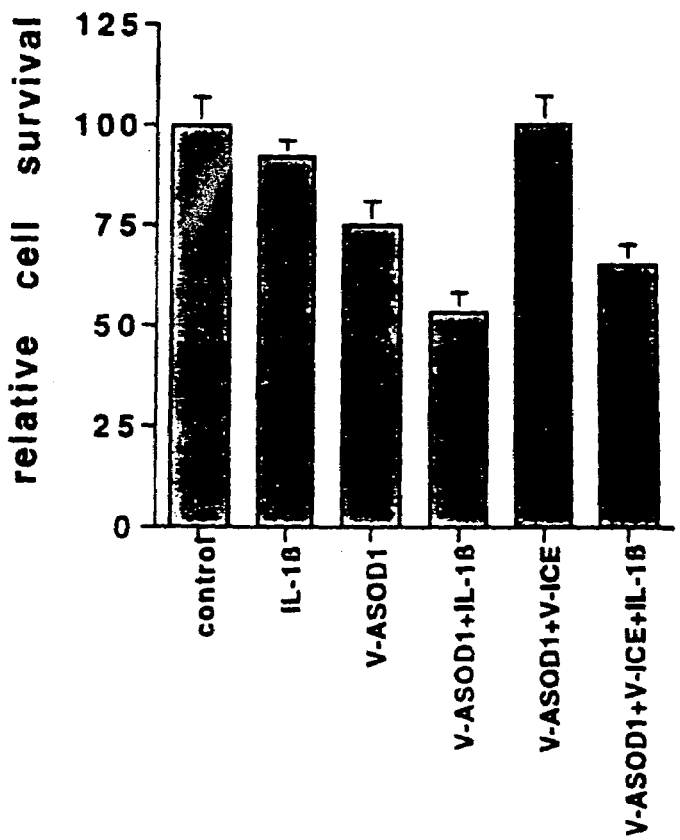

The disparity in effects afforded by blocking IL-1β or the IL-1 receptor in the two paradigms raised the issue of whether IL-1β secretion is differentially affected. When SOD1 is down-regulated there is an almost 3-fold increase in IL-1β secretion per cell at 24 h, an increase which is blocked by $V-ICE_{inh}$ (FIG. 5C). Upon withdrawal of trophic support there is no increase in IL-1β secretion at 24 h; in contrast cells treated with NGF manifest a 4-fold increase in IL-1β secretion (FIG. 5C). Similar trends were observed at 6 h of treatment in both paradigms.

The effectiveness of IL-1β blockade in protecting cells against SOD1 down-regulation led us to determine the effect of exogenous IL-1β in this paradigm. IL-1β itself has no effect, however IL-1β in conjunction with V-ASOD1 potentiates the cell death. IL-1β also abrogates the protection provided by $V-ICE_{inh}$.

Discussion:

Both the lack of trophic factors and damage by free radicals have been invoked as possible contributors to cell shrinkage and loss in neurodegenerative disorders including Parkinson's disease and Alzheimer's disease. In the studies presented here a single model neuronal culture system has been used to compare pathways leading to cell death resulting from either trophic factor withdrawal or from free radical damage following down-regulation of the copper-zinc superoxide dismutase. These pathways are quite divergent in their initial steps. For example, survival after trophic factor deprivation is promoted by cyclic AMP analogs (Rukenstein et al., 1991), N-acetylcysteine (Ferrari et al., 1995) and by nitric oxide generators (Farinelli et al., 1995) as well as by serum and growth factors (Rukenstein et al., 1991 and Pittman et al., 1993) but not by vitamin E (Ferrari et al., 1995). By comparison, cells are protected from SOD1 down-regulation by inhibitors of nitric oxide synthesis and by vitamin E (Troy and Shelanski, 1994), while death is unaffected by cAMP, growth factors (Troy and Shelanski, 1994), serum and N-acetylcysteine and enhanced by nitric oxide generators.

It has been previously demonstrated that inhibition of ICE-family proteases by crm-A protects neurons from trophic factor withdrawal (Gagliardini et al., 1994). By using a novel protease inhibitor designed to inhibit all members of the ICE family it is demonstrated herein that the same family of proteases is involved in free-radical induced apoptosis, suggesting that there is a shared downstream pathway leading to death from these two initially divergent causes. This finding of commonality is in agreement with earlier data showing that expression of bcl-2 also protects in both paradigms (Farinelli et al., 1995), as well as in a variety of systems in which cell death is initiated by different means (Korsmeyer, 1992a and Korsmeyer, 1992b). These recent findings indicate that PC12 cell death initiated by SOD1 down-regulation is dependent on generation of nitric oxide and therefore apparently on formation of peroxynitrite. The inhibition of cell loss by ICE family inhibitors suggests that free radicals such as peroxynitrite themselves do not directly cause apoptotic death, but, more likely, that they function as signals that initiate a common death pathway.

Despite the presence of what appears to be a broadly shared final route to apoptosis, the data presented herein indicate that even this "final pathway" may show individuality, depending on the initiating causes of death. For example, significant distinctions were noted in the concentrations of ICE family inhibitors at which protection was obtained in the different paradigms presented herein. Cells were protected from SOD1 down-regulation at concentrations of V-ICE$_{inh}$ nearly an order of magnitude lower than those required to save them from trophic factor withdrawal. There was a comparable difference in the potency of ZVAD-FMK (Seq. I.D. No. 2) in the two systems. In addition, ZYVAD-CMK (Seq. I.D. No. 6) fully protected from SOD1 down-regulation while providing only partial protection from trophic deprivation, even at five-fold higher levels. For sympathetic neurons, cell death evoked by NGF deprivation was abrogated by V-ICE$_{inh}$ and ZVAD-FMK (Seq. I.D. No. 2) but was unaffected by ZYVAD-CMK (Seq. I.D. No. 6). It should be noted that ZYVAD-CMK (Seq. I.D. No. 6) would be expected to be more specific as an inhibitor of ICE, while ZVAD-CMK (Seq I.D. No. 2) may more generally inhibit ICE family proteases (Nicholson et al., 1995). These differences in the efficacy of these compounds in the two paradigms may reflect the involvement of different members of the ICE-family of proteases in each pathway, the availability of different substrates or a combination of the two.

The demonstration that the ICE family of proteases is involved in apoptosis in the models used here led to an investigation of the role of IL-1β itself. Once again differences in the "final pathway" are apparent. Both a blocking antibody to IL-1β and the naturally occurring IL-1 receptor antagonist, IL-1ra, provide almost complete protection against SOD1 down-regulation. In contrast, the blocking antibody failed to protect against trophic factor withdrawal and IL-1ra protected partially, but only at extremely high levels. Although there is an increase of IL-1β release after SOD1 down-regulation, there was no detectable change after withdrawal of trophic support. This rules out the possibility that loss of trophic support triggers a massive release of IL-1β that can be blocked only by enhanced concentrations of ICE inhibitors or that cannot be blocked by the levels of antibody or receptor antagonist that were employed. Moreover, it was noted that the largest increase in IL-1β release occurs after exposure to NGF. Because NGF prevents rather than causes death of PC12 cells deprived of trophic support, it appears that enhanced IL-1β production is not sufficient to evoke death in this system. Consistent with this, addition of 1 μg/ml rhIL-1β to PC12 cultures in the presence of NGF, insulin, or serum did not produce cell death. Therefore, apoptosis triggered by down-regulation of SOD1 does not appear due to increased secretion of IL-1β alone, but rather to an increased vulnerability to this cytokine. This could stem from a variety of mechanisms including enhanced IL-1β responsiveness. Another possible mechanism is by increased production of nitric oxide. Il-1β induces nitric oxide production in pancreatic cells. It has been shown that generation of nitric oxide enhances the death mediated by the down-regulation of SOD1, whereas nitric oxide is protective against serum-deprivation mediated apoptosis. The generation of nitric oxide by IL-1β may account for the differential effects of block of IL-1β on these systems.

Although it is tempting to exclude IL-1β as a major factor in death caused by trophic factor deprivation in the model system, another possibility cannot be ruled out. It is possible that loss of trophic support makes the cells so exquisitely sensitive to even basal levels of this interleukin that blockade can only be achieved by extremely high antibody and receptor antagonist levels.

In spite of the differences in the specifics of the final steps leading to cell death in the two paradigms tested, the data show the possibility of designing agents which could block cell loss in neurodegenerations of diverse etiology. For example, the novel inhibitor, V-ICE$_{ins}$ which was used in these experiments would be expected to inhibit all ICE family proteases by denying them access to their substrates. This differs from pseudosubstrate inhibitors such as those based on the YVAD (Seq. I.D. No. 7) or DVED (Seq. I.D. No. 8) motifs which distinguish between individual members of the ICE protease family by mimicking the cleavage site of the substrate (Nicholson et al., 1995). In additional contrast to pseudosubstrate inhibitors, V-ICE$_{inh}$ should also avoid the problem of inhibiting non-ICE cysteine proteases. Although in these experiments, a general substrate-directed inhibitor of ICE family proteases (V-ICE$_{inh}$) was purposely designed, the Antennapedia-linked vector should also be useful for facilitating internalization of pseudosubstrate ICE family inhibitors. Thus, this technology might be useful to target either all, or single members of the ICE protease family. V-ICE$_{inh}$ may therefore be viewed as a prototype of a potential new class of therapeutic agents.

The demonstration of a role for IL-1β in apoptosis induced by free radicals might have particular relevance to Alzheimer's Disease. The brains of patients dying from this disease have been reported to have elevated levels of IL-1 (Griffin et al., 1989). Several recent reports have raised the possibility that free radical generation by glycated tau (Yan et al., 1994), amyloid (Hensley et al., 1994) or both can occur in these brains. If this is the mechanism by which cell damage and loss occurs, it is likely that agents such as V-ICE$_{inh}$, which block ICE activity and anti-inflammatory agents which block IL-1 might be useful in the treatment of the disease. The latter have already been reported to show promise in preliminary clinical studies (Breitner et al., 1994; McGeer et al., 1992; and McGeer and Rogers, 1992).

REFERENCES

Adams, M. D. et al., (1995) *Nature* 377, 3–17.
Baron et al., (1982) *Cell* 28, 395–404.
Batistatou, A. & Greene, L. A. (1991) *J. Cell Biol.* 115, Batistatou, A., Merry, D. E., Korsmeyer, S. J. & Greene, L. A. (1993) *J. Neurosci.* 13, 4422–4428.

Blondelle, S. E. et al., (1994) *Antimicrobial Agents and Chemotherapy* 38, 2280–2286.

Bock, M. G. et al., (1992) *Journal of Controlled Release* 21, 73–80.

Boudreau, N., Sympson, C. J., Werb, Z. & Bissell, M. J. (1995) *Science* 267, 891–893.

Breitner, J. C. S., Gau, B. A., Welsh, K. A., Plassman, B. L., McDonald, W. M., Helms, M. J. & Anthony, J. C. (1994) *Neurology.* 44, 227–232.

Coyle, J. T. & Puttfarcken, P. (1993) *Science* 262, 689–695.

Dressman et al., (1982) *Nature* 295, 185–160.

Enari, M., Hug, H. & Nagata, S. (1995) *Nature* 375, 78–81.

Farinelli, S. E., Joyce, M. P. & Greene, L. A. (1995) *Soc. for Neurosci.* 21, 1787.

Fernandes-Alnemri, T., Litwack, G. & Alnemri, E. S. (1994) *J. Biol. Chem.* 269, 30761–30764.

Ferrari, G. & Greene, L. A. (1994) *EMBO J.* 13, 5922–5928. 461–471.

Ferrari G., Yan C. Y. I. & Greene, L. A. (1995) *J. Neurosci.* 15, 2857–2866.

Gagliardini, V., Fernandez, P-A., Lee, R. K. K., Drexler, H. C. A., Rotello, R. J., Fishman, M. C. & Yuan, J. (1994) *Science* 263, 826–828.

Griffin, W. S. T., Stanley, L. C. & Ling, C. (1989) *Proc. Natl. Acad. Sci. USA* 86, 7611–7615.

Greene, L. A. & Tischler, A. S. (1976) *Proc. Natl. Acad. Sci. U.S.A.* 73, 2424–2428.

Hengartner, M. O., Ellis, R. E. & Horvitz, H. R. (1992) *Nature* 356, 494–499.

Hensley, K., Carney, J. M., Mattson, M. P., Aksenova, M., Harris, M., Wu, J. F., Floyd, R. A. and Butterfield, D. A. (1994) *Proc. Natl. Acad. Sci. USA* 91, 3270–3274.

Kaiser et al. (1984) *Science* 223 249–255.

Kempf et al. (1991) *Intl. J. Peptide and Prot. Res.* 38, 237–241.

Korsmeyer S. J. (1992a) *Immunol. Today.* 13: 285–288.

Korsmeyer S. J. (1992b) *Blood.* 80: 879–886.

Kuida, K., Lippke, J. A., Ku, G., Harding, M. W., Livingston, D. J., Su, M. S.-S. & Flavell, R. A. (1995) *Science* 267, 2000–2003.

Kumar, S., Knioshita, M., Noda, M., Copeland, N. G. & Jenkins, N. A. (1994) *Genes & Develop.* 8, 1613–1626.

Laemmli, U. K. (1970) *Nature* 227, 680–685.

Lazebnik, Y. A., Kaufmann, S. H., Desnoyers, S., Poiriers, G. G. & Earnshaw, W. C. (1994) *Nature* 371, 346–347.

Lee, J. Barrett, R. E. and Bovy, P. R. (1995) *Letters in Peptide Science* 2, 253–258.

Lerner et al., *Cell* 23, 309–310 (1981);

Lerner, (1983) *Scientific American* 248, 66–74.

Los, M., Van de Craen, M., Penning, L. C., Shenk H., Westendorp, M., Baeuerle, P. A., Droge, W., Krammer, P. H., Fiers, W. & Schulze-Osthoff, K. (1995) *Nature* 375, 81–83.

McGeer, P. L., McGeer, E.,Rogers, J. & Sibley, J. (1992) *Lancet* 335, 1037.

McGeer, P. L. & Rogers, J. (1992) *Neurology* 42, 447–449.

Ankarcrona, M., Dypbukt, J. M., Brune, B & Nicotera, P. (1994) *Exp. Cell Res.* 213, 172–177.

Milligan, C. E., Prevette, D., Yaginuma, H., Homma, S., Cardwell, C., Fritz, L. C., Tomaselli, K. J., Oppenheim, R. W. & Schwartz, L. M. (1995) *Neuron* 15, 385–393.

Miura, M., Zhu, H., Rotello, R., Hartweig, E. A. & Yuan, J. (1994) *Cell* 75, 653–660.

Nicholson, D. W., Ali, A., Thornberry, N. A., Vaillancourt, J. P., Ding, C. K., Gallant, M., Gareau, Y., Griffin, P. R., Labelle, M., Lazabnik, Y., Munday, N. A., Raju, S. M., Smulson, M. E., Yamin, T.-T., Yu, V. L. & Miller, D. K. (1995) *Nature* 376, 37–43.

Ojala, W. H., Ojala, C. R. and Gleason, W. B. (1995) *Antiviral Chemistry and Chemotherapy* 6, 25–33.

Pinilla, C., et al. (1995) *Peptide Science* 37, 221–240.

Pittman, R. N., Wang, S., DiBenedetto, A. J. & Mills, J. C. (1993) *J. Neurosci.* 13, 3669–3680.

Prochiantz, A. & Theodore, L. (1995) *Bioessays* 17, 39-Ross et al., (1981) *Nature,* 294, 654–658.

Rukenstein, A., Rydel, R. E. & Greene, L. A. (1991) *J. Neurosci.* 11, 2552–2563.

Rydel, R. E. & Greene, L. A. (1988) *Proc. Natl. Acad. Sci. USA* 85, 1257–1261.

Shaw, E. (1990) in Advances in Enzymology, ed. Meister, A. (John Wiley & Sons, New York), pp. 271–347.

Tewari, M. & Dixit, V. M. (1995) *J. Biol. Chem.* 270, 3255–3260.

Tewari, M., Beidler, D. R. & Dixit, V. M. (1995) *J. Biol. Chem.* 270, 18738–18741.

Tewari, M., Quan, L. T., O'Rourke, K., Desnoyers, S., Zeng, Z., Beidler, D. R., Poirier, G. G., Salvesen, G. S. & Dixit, V. M. (1995) *Cell* 81, 801–809.

Thornberry, N. A. (1994) *Methods in Enzymology* 244, 615–631.

Troy, C. M. & Shelanski, M. L. (1994) *Proc. Natl. Acad. Sci. USA* 91, 6384–6387.

Walter et al., (1981) *Proc. Natl. Acad. Sci. USA* 78, 4882–4886.

Wang, L., Miura, M., Bergeron, L., Zhu, H., & Yuan, J. (1994) *Cell* 78, 739–750.

Wong et al., (1982) *Proc. Natl. Sci. USA* 79, 5322–5326.

Yan, S. D., Brett, J., Godman, G., Zou, Y. S., Scott, C. W., Caputo, C., Frappier T., Smith, M. A. et al. (1994) *Proc. Natl. Acad. Sci. USA* 91, 7787–7791.

Yuan, J., Shahan, S., Ledoux, S., Ellis, H. M. & Horvitz, H. R. (1993) *Cell* 74, 641–652.

What is claimed is:

1. A compound having the structure:

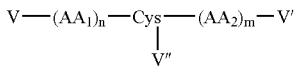

wherein n=0,1,2,3,4 or 5 and m=0,1,2,3,4 or 5, provided the sum of (n+m) is greater than or equal to two and less than or equal to five,
if n=1, $(AA_1)_n$=Ala-,
if n=2, $(AA_1)_n$=Gln-Ala-,
if n≧3, $(AA_1)_n$=$(Xaa)_p$-Gln-Ala-,
and Xaa=any amino acid and
wherein if n=3, p=1,
if n=4, p=2,
if n=5, p=3,
if m=1, $(AA_2)_m$=-Arg,
if m=2, $(AA_2)_m$=-Arg-Gly,
if m≧3, $(AA_2)_m$=-Arg-Gly-$(Xaa)_q$,
wherein if m=3, q=1,
if m=4, q=2,
if m=5, q=3, wherein each V, V' or V" is independently an agent capable of specifically directing the compound to a cell.

2. The compound of claim 1, wherein V, V' or V" is a polypeptide comprising at least a portion of an Antennepedia polypeptide.

3. The compound of claim 2, wherein V, V' or V" is at least a portion of a polypeptide comprising the sequence NPyS-Arg-Gln-Ile-Lys-Ile-Trp-Phe-Gln-Asn-Arg-Arg-Met-Lys-Trp-Lys-Lys-(Seq. I.D. No. 9).

4. The compound of claim 3, wherein the compound is NPyS-Arg-Gln-Ile-Lys-Ile-Trp-Phe-Gln-Asn-Arg-Arg-Met-Lys-Trp-Lys-Lys-Ile-Gln-Ala-Cys-Arg-Gly (Seq. I.D. No. 10).

5. The compound of claim 3, wherein the compound is NPyS-Arg-Gln-Ile-Lys-Ile-Trp-Phe-Gln-Asn-Arg-Arg-Met-Lys-Trp-Lys-Lys-Gln-Ala-Cys-Arg-Gly (Seq. I.D. No. 11).

6. The compound of claim 1, wherein each V, V' or V" is independently an antibody, an adjuvant or a cell-specific ligand.

7. The compound of claim 1, wherein the cell is a neuronal cell, a cardiac cell or a liver cell.

* * * * *

SEQUENCE LISTING

<160> NUMBER OF SEQ ID NOS: 11

<210> SEQ ID NO 1
<211> LENGTH: 6
<212> TYPE: PRT
<213> ORGANISM: artificial sequence

```
<220> FEATURE:
<223> OTHER INFORMATION: COMPETITIVE INHIBITOR OF ICE

<400> SEQUENCE: 1

Ile Gln Ala Cys Arg Gly
1               5

<210> SEQ ID NO 2
<211> LENGTH: 4
<212> TYPE: PRT
<213> ORGANISM: artificial sequence
<220> FEATURE:
<223> OTHER INFORMATION: COMPETITIVE INHIBITOR OF ICE

<400> SEQUENCE: 2

Glx Val Ala Asp
1

<210> SEQ ID NO 3
<211> LENGTH: 5
<212> TYPE: PRT
<213> ORGANISM: artificial sequence
<220> FEATURE:
<223> OTHER INFORMATION: COMPETITIVE INHIBITOR OF ICE

<400> SEQUENCE: 3

Gln Ala Cys Arg Gly
1               5

<210> SEQ ID NO 4
<211> LENGTH: 6
<212> TYPE: PRT
<213> ORGANISM: artificial sequence
<220> FEATURE:
<223> OTHER INFORMATION: CONTROL PEPTIDE

<400> SEQUENCE: 4

Gly Arg Cys Ala Gln Ile
1               5

<210> SEQ ID NO 5
<211> LENGTH: 6
<212> TYPE: PRT
<213> ORGANISM: artificial sequence
<220> FEATURE:
<223> OTHER INFORMATION: CONTROL PEPTIDE

<400> SEQUENCE: 5

Ile Cys Gly Arg Gln Ala
1               5

<210> SEQ ID NO 6
<211> LENGTH: 5
<212> TYPE: PRT
<213> ORGANISM: artificial sequence
<220> FEATURE:
<223> OTHER INFORMATION: COMPETITIVE INHIBITOR OF ICE

<400> SEQUENCE: 6

Glx Tyr Val Ala Asp
1               5

<210> SEQ ID NO 7
<211> LENGTH: 4
<212> TYPE: PRT
<213> ORGANISM: artificial sequence
<220> FEATURE:
```

-continued

```
<223> OTHER INFORMATION: MOTIF OF PSEUDOSUBSTRATE INHIBITOR

<400> SEQUENCE: 7

Tyr Val Ala Asp
1

<210> SEQ ID NO 8
<211> LENGTH: 4
<212> TYPE: PRT
<213> ORGANISM: artificial sequence
<220> FEATURE:
<223> OTHER INFORMATION: MOTIF  OF PSEUDOSUBSTRATE INHIBITORS

<400> SEQUENCE: 8

Asp Val Glu Asp
1

<210> SEQ ID NO 9
<211> LENGTH: 16
<212> TYPE: PRT
<213> ORGANISM: artificial sequence
<220> FEATURE:
<223> OTHER INFORMATION: PORTION OF ANTENNEPEDIA POLYPEPTIDE

<400> SEQUENCE: 9

Arg Gln Ile Lys Ile Trp Phe Gln Asn Arg Arg Met Lys Trp Lys Lys
1               5                   10                  15

<210> SEQ ID NO 10
<211> LENGTH: 22
<212> TYPE: PRT
<213> ORGANISM: artificial sequence
<220> FEATURE:
<223> OTHER INFORMATION: PORTION OF ANTENNEPEDIA POLYPEPTIDE

<400> SEQUENCE: 10

Arg Gln Ile Lys Ile Trp Phe Gln Asn Arg Arg Met Lys Trp Lys Lys
1               5                   10                  15

Ile Gln Ala Cys Arg Gly
            20

<210> SEQ ID NO 11
<211> LENGTH: 21
<212> TYPE: PRT
<213> ORGANISM: artificial sequence
<220> FEATURE:
<223> OTHER INFORMATION: PORTION OF ANTENNEPEDIA POLYPEPTIDE

<400> SEQUENCE: 11

Arg Gln Ile Lys Ile Trp Phe Gln Asn Arg Arg Met Lys Trp Lys Lys
1               5                   10                  15

Gln Ala Cys Arg Gly
            20
```